(12) United States Patent
Olek et al.

(10) Patent No.: US 7,524,629 B2
(45) Date of Patent: Apr. 28, 2009

(54) METHOD FOR DETECTING CYTOSINE METHYLATION IN DNA SAMPLES

(75) Inventors: Alexander Olek, Berlin (DE); Kurt Berlin, Stahnsdorf (DE)

(73) Assignee: Epigenomics AG, Berlin (DE)

( * ) Notice: Subject to any disclaimer, the term of this patent is extended or adjusted under 35 U.S.C. 154(b) by 173 days.

(21) Appl. No.: 10/220,090

(22) PCT Filed: Feb. 23, 2001

(86) PCT No.: PCT/DE01/00750

§ 371 (c)(1),
(2), (4) Date: Dec. 30, 2002

(87) PCT Pub. No.: WO01/62064

PCT Pub. Date: Aug. 30, 2001

(65) Prior Publication Data

US 2003/0129620 A1   Jul. 10, 2003

(30) Foreign Application Priority Data

Feb. 25, 2000   (DE) .............................. 100 10 280

(51) Int. Cl.
*C07H 21/04* (2006.01)
*C07H 21/02* (2006.01)
*C12Q 1/68* (2006.01)

(52) U.S. Cl. .................... 435/6; 435/91.2; 435/91.1; 435/287.2

(58) Field of Classification Search .............. 435/6, 435/91.1, 91.2; 536/23.1, 24.3
See application file for complete search history.

(56) References Cited

U.S. PATENT DOCUMENTS

| 5,605,798 A | 2/1997 | Koster | |
|---|---|---|---|
| 5,728,526 A | 3/1998 | George, Jr. et al. | |
| 5,976,802 A * | 11/1999 | Ansorge et al. | 435/6 |
| 6,013,431 A * | 1/2000 | Soderlund et al. | 435/5 |
| 6,214,556 B1 * | 4/2001 | Olek et al. | 435/6 |
| 6,251,594 B1 * | 6/2001 | Gonzalgo et al. | 435/6 |
| 2003/0119025 A1 | 6/2003 | Olek et al. | |

FOREIGN PATENT DOCUMENTS

| WO | WO 95/00669 A | 1/1995 |
|---|---|---|
| WO | WO 98/44151 A | 10/1998 |
| WO | WO 98/56952 A | 12/1998 |
| WO | WO 99/28498 * | 6/1999 |
| WO | WO 99/28498 A | 6/1999 |
| WO | WO 99/55905 A | 11/1999 |
| WO | WO 99/58721 A | 11/1999 |
| WO | WO 99/67414 A1 | 12/1999 |

OTHER PUBLICATIONS

Gonzalgo et al. (Nucleic Acids Research, vol. 25, No. 12, pp. 2529-2531, 1997).*
Pastinen et al. (Clinical Chemistry, vol. 42, No. 9, pp. 1391-1397, 1996).*
Nikiforov et al. (Nucleic Acids Research, vol. 22, No. 20, pp. 4167-4175, 1994).*
Yoshihashi et al. (Am. J. of Human Genetics, vol. 67, No. 4, pp. 1335-1335, Oct. 2000).*
Ayyadevara et al. (Analytical Biochemistry, vol. 284, pp. 11-18, 2000).*
Nyren et al. (Analytical Biochemistry, Voo. 244, pp. 367-373, 1997).*
Grigg et al., "Sequencing 5-Methylcytosine Residues in Genomic DNA," Bioessays, 16(6):431-6 (1994).
Rein et al., "Identifying 5-methylcytosine and related modifications in DNA genomes," Nucleic Acids Research, 26(10):2255-64 (1998).
Paul et al., "Cytosine Methylation: Quantitation by Automated Genomic Sequencing and GENESCANtm Analysis," Biotechniques, 21:126-33 (1996).
Niemeyer et al., "DNA Microarrays," Angew. Chem. Int. Ed., 38(19):3039-43 (1999).
Grunau et al., "Bisulfite genomic sequencing: systematic investigation of critical experimental parameters," Nucleic Acids Research, 29(13):e65 (pp. 1-7) (2001).
Rein et al., "Active Mammalian Replication Origins Are Associated with a High-Density Cluster of mCpG Dinucleotides," Molecular and Cellular Biology, 17(1):416-26 (1997).

* cited by examiner

*Primary Examiner*—Jeanine A Goldberg
(74) *Attorney, Agent, or Firm*—Kriegsman & Kriegsman

(57) ABSTRACT

Described is a method for detecting 5-methylcytosine in genomic DNA samples. First, a genomic DNA from a DNA sample is chemically converted with a reagent, 5-methylcytosine and cytosine reacting differently, and the pretreated DNA is subsequently amplified using a polymerase and at least one primer. In the next step, the amplified genomic DNA is hybridized to at least one oligonucleotide, forming a duplex, and said oligonucleotide is elongated by at least one nucleotide, the nucleotide carrying a detectable label, and the elongation depending on the methylation status of the specific cytosine in the genomic DNA sample. In the next step, the elongated oligonucleotides are analyzed for the presence of the label.

29 Claims, No Drawings

METHOD FOR DETECTING CYTOSINE METHYLATION IN DNA SAMPLES

The present invention relates to a method for detecting 5-methylcytosine in genomic DNA samples. The present invention describes a method for detecting the metylation status of genomic DNA samples. The method can, at the same time, also be used for detecting point mutations and single nucleotide polymorphisms (SNPs).

The levels of observation that have been well studied by the methodological developments of recent years in molecular biology include the gene itself, the translation of genes in RNA, and the resulting proteins. The question of which gene is switched on at which point in the course of the development of an individual, and the question of how the activation and inhibition of specific genes in specific cells and tissues are controlled is correlatable to the degree and character of methylation of genes or of the genome. In this respect, the assumption suggests itself that pathogenic conditions express themselves in an altered methylation pattern of individual genes or of the genome.

5-methylcytosine is the most frequent covalently modifiable base in the DNA of eukaryotic cells. It plays a role, for example, in the regulation of the transcription, in genetic imprinting, and in tumorigenesis. Therefore, the identification of 5-methylcytosine as a part of genetic information is of considerable interest. However, 5-methylcytosine positions cannot be identified by sequencing since 5-methylcytosine has the same base pairing behavior as cytosine. Moreover, the epigenetic information carried by the 5-methylcytosines is completely lost during a PCR amplification.

A relatively new and now the most frequently used method for analyzing DNA for 5-methylcytosine is based on the specific reaction of bisulfite with cytosine which, upon subsequent alkaline hydrolysis, is converted to uracil which corresponds to thymidine in its base pairing behavior. However, 5-methylcytosine remains unmodified under these conditions. Consequently, the original DNA is converted in such a manner that methylcytosine, which originally cannot be distinguished from cytosine in its hybridization behavior, can now be detected as the only remaining cytosine using "normal" molecular biological techniques, for example, by amplification and hybridization or sequencing. All these techniques are based on base pairing which is now taken full advantage of. The Prior Art is defined in terms of sensitivity by a method which encloses the DNA to be analyzed in an agarose matrix, thus preventing the diffusion and renaturation of the DNA (bisulfite reacts only on single-stranded DNA), and which replaces all precipitation and purification steps with fast dialysis (Olek, A. et al, Nucl. Acids. Res. 1996, 24, 5064-5066). Using this method, it is possible to analyze individual cells, which illustrates the potential of the method. Up to now, however, only individual regions of a length of up to approximately 3000 base pairs are analyzed; a global analysis of cells for thousands of possible methylation analyses is not possible. However, this method cannot reliably analyze very small fragments from small sample quantities either. These are lost in spite of the diffusion protection by the matrix.

An overview of the further known possibilities of detecting 5-methylcytosines can be gathered from the following survey article: Rein, T., DePamphilis, M. L., Zorbas, H., Nucleic Acids Res. 1998, 26, 2255.

Up to now, the bisulfite technology is only used in research with few exceptions (e.g., Zeschnigk M. et al, Eur J Hum Genet. 1997, 5, 94-98). Always, however, short specific fragments of a known gene are amplified subsequent to a bisulfite treatment and either completely sequenced (Olek, A. and Walter, J., Nat Genet. 1997, 17, 275-276) or individual cytosine positions are detected by a primer extension reaction (Gonzalgo, M. L., and Jones, P. A., Nucl. Acids Res. 1997, 25, 2529-2531, WO 9500669) or by an enzymatic digestion (Xiong, Z. and Laird, P. W., Nucl. Acids. Res. 1997, 25, 2532-2534). In addition, the detection by hybridization has also been described (Olek et al., WO 99 28498).

Further publications dealing with the use of the bisulfite technique for methylation detection in individual genes are: Xiong, Z. and Laird, P. W. (1997), Nucl. Acids Res. 25, 2532; Gonzalgo, M. L. and Jones, P. A. (1997), Nucl. Acids Res. 25, 2529; Grigg, S. and Clark, S. (1994), Bioassays 16, 431; Zeschnik, M. et al. (1997), Human Molecular Genetics 6, 387; Teil, R. et al. (1994), Nucl. Acids Res. 22, 695; Martin, V. et al. (1995), Gene 157, 261; WO 97 46705; WO 95 15373 and WO 45560.

An overview of the Prior Art in oligomer array manufacturing can be gathered from a special edition of Nature Genetics (Nature Genetics Supplement, Volume 21, January 1999), published in January 1999, and from the literature cited therein.

There are different methods for immobilizing DNA. The best-known method is the fixed binding of a DNA which is functionalized with biotin to a streptavidin-coated surface (Uhlen, M. et al. 1988, Nucleic Acids Res. 16, 3025-3038). The binding strength of this system corresponds to that of a covalent chemical bond without being one. To be able to covalently bind a target DNA to a chemically prepared surface, a corresponding functionality of the target DNA is required. DNA itself does not possess any functionalization which is suitable. There are different variants of introducing a suitable functionalization into a target DNA: two functionalizations which are easy to handle are primary aliphatic amines and thiols. Such amines are quantitatively converted with N-hydroxysuccinimide esters, and thiols react quantitatively with alkyl iodides under suitable conditions. A difficulty consists in introducing such a functionalization into a DNA. The simplest variant is the introduction via a primer of a PCR. Disclosed variants use 5'-modified primers ($NH_2$ and SH) and a bifunctional linker.

An essential component of the immobilization on a surface is its constitution. Systems described up to now are mainly composed of silicon or metal. A further method of binding a target DNA is based on the use of a short recognition sequence (e.g., 20 bases) in the target DNA for hybridization to a surface-immobilized oligonucleotide. Enzymatic variants for introducing chemically activated positions in a target DNA have been described as well. In this case, a 5'-$NH_2$-functionalization is carried out enzymatically on a target DNA.

For scanning an immobilized DNA array, fluorescently labeled probes have often been used. Particularly suitable for fluorescence labeling is the simple attachment of Cy3 and Cy5 dyes to the 5'-OH of the specific probe. The detection of the fluorescence of the hybridized probes is carried out, for example via a confocal microscope. Cy3 and Cy5 dyes, besides many others, are commercially available.

An overview of the Prior Art in oligomer array manufacturing can be gathered from a special edition of Nature Genetics (Nature Genetics Supplement, Volume 21, January 1999), published in January 1999, and from the literature cited there, as well as from U.S. Pat. No. 5,994,065 on methods for preparing solid supports for target molecules such a oligonucleotides involving reduced, non-specific background signal.

More recent methods for detecting mutations are specified in the following:

Worth mentioning as a special case of sequencing is the single-base primer extension (Genetic Bit Analysis) (Head, S R., Rogers, Y H., Parikh K., Lan, G., Anderson, S., Goelet, P., Boycejacino M T., Nucleic Acids Research. 25(24): 5065-5071, 1997; Picoult-Newberg, L., Genome Res. 9(2): 167-174, 1999). A combined amplification and sequencing is described in U.S. Pat. No. 5,928,906 where a base-specific termination on matrix molecules is used. A further method uses a ligase/polymerase reaction for identifying nucleotides (U.S. Pat. No. 5,952,174).

Matrix Assisted Laser Desorption Ionization Mass Spectrometry (MALDI) is a very efficient development for the analysis of biomolecules (Karas, M. and Hillenkamp, F. (1988), Laser desorption ionization of proteins with molecular masses exceeding 10000 daltons. Anal. Chem. 60: 2299-2301). An analyte is embedded in a light-absorbing matrix. By a short laser pulse, the matrix is evaporated, thus transporting the analyte molecule into the vapor phase in an unfragmented manner. The analyte is ionized by collisions with matrix molecules. An applied voltage accelerates the ions into a field-free flight tube. Due to their different masses, the ions are accelerated at different rates. Smaller ions reach the detector sooner than bigger ones.

Matrix Assisted Laser Desorption Ionization Mass Spectrometry (MALDI) is a very efficient method for the analysis of biomolecules (Karas, M. and Hillenkamp, F. (1988), Laser desorption ionization of proteins with molecular masses exceeding 10000 daltons. Anal. Chem. 60: 2299-2301). An analyte is embedded in a light-absorbing matrix. Using a short laser pulse, the matrix is evaporated, thus transporting the analyte molecule into the vapor phase in an unfragmented manner. The analyte is ionized by collisions with matrix molecules. An applied voltage accelerates the ions into a field-free flight tube. Due to their different masses, the ions are accelerated at different rates. Smaller ions reach the detector sooner than larger ones.

MALDI is ideally suited to the analysis of peptides and proteins. The analysis of nucleic acids is somewhat more difficult (Gut, I. G. and Beck, S. (1995), DNA and Matrix Assisted Laser Desorption Ionization Mass Spectrometry. Molecular Biology: Current Innovations and Future Trends 1: 147-157.). The sensitivity for nucleic acids is approximately 100 times worse than for peptides and decreases disproportionally with increasing fragment size. For nucleic acids having a multiply negatively charged backbone, the ionization process via the matrix is considerably less efficient. For MALDI, the selection of the matrix plays an eminently important role. For the desorption of peptides, several very efficient matrixes have been found which produce a very fine crystallization. For DNA, there are currently several matrixes in use, however, this has not altered the difference in sensitivity. The difference in sensitivity can be reduced by chemically modifying the DNA in such a manner that it becomes more similar to a peptide. Phosphorothioate nucleic acids in which the usual phosphates of the backbone are substituted by thiophosphates can be converted into a charge-neutral DNA using simple alkylation chemistry (Gut, I. G. and Beck, S. (1995), A procedure for selective DNA alkylation and detection by mass spectrometry. Nucleic Acids Res. 23: 1367-1373). The coupling of a charge tag to this modified DNA results in an increase in sensitivity by the same amount as that found for peptides. A further advantage of charge tagging is the increased stability of the analysis against impurities which make the detection of unmodified substrates considerably more difficult.

Genomic DNA is obtained from DNA of cell, tissue or other test samples using standard methods. This standard methodology is found in references such as Fritsch and Maniatis eds., Molecular Cloning: A Laboratory Manual, 1989.

Mutualities between promoters consist not only in the occurrence of TATA- or GC-boxes but also for which transcription factors they possess binding sites and at what distance these are located from each other. The existing binding sites for a specific protein do not match completely in their sequence but conserved sequences of at least 4 bases are found which can still be elongated by inserting wobbles, i.e., positions at which in each case different bases are located. Moreover, these binding sites are present at specific distances from each other.

However, the distribution of the DNA in the interphase chromatin which occupies the largest portion of the nuclear volume is subject to a very special arrangement. Thus, the DNA is attached to the nuclear matrix, a filamentous pattern at the inner side of the nuclear membrane, at several locations. These regions are designated as matrix attachment regions (MAR) or scaffold attachment regions (SAR). The attachment has an essential influence on the transcription or the replication. These MAR fragments have no conserved sequences but to 70% they consist of A or T, and are located in the vicinity of cis-acting regions which regulate the transcription in a general manner, and in the vicinity of topoisomerase II recognition sites.

In addition to promoters and enhancers, further regulatory elements, so-called "insulators", exist for different genes. These insulators can, for example, inhibit the action of the enhancer on the promoter if they are located between enhancer and promoter, or else, if located between heterochromatin and a gene, can protect the active gene from the influence of the heterochromatin. Examples of such insulators include: firstly, so-called "LCR" (locus control regions) consisting of several sites which are hypersensitive to DNAase I; secondly, certain sequences such as SCS (specialized chromatin structures) or SCS', 350 or 200 bp long, respectively, and highly resistant to degradation by DNAase I, and flanked on both sides with hypersensitive sites (distance in each case 100 bp). The protein BEAF-32 binds to scs'. These insulators can be located on both sides of the gene.

It is the aim of the present invention to provide a method particularly suitable for concurrently detecting cytosine methylations and SNPs in genomic DNA samples. In this process, it should preferably be possible for a plurality of fragments to be analyzed concurrently.

The aim of the invention is reached by a method for detecting 5-methylcytosine in genomic DNA samples, wherein the following steps are carried out:

(a) a genomic DNA from a DNA sample is chemically converted with a reagent, 5-methylcytosine and cytosine reacting differently, thus exhibiting different base pairing behaviors in the DNA duplex subsequent to the reaction;

(b) the pretreated DNA is amplified using a polymerase and at least one oligonucleotide (type A) as a primer;

(c) the amplified genomic DNA is hybridized to at least one oligonucleotide (type B), forming a duplex, said hybridized oligonucleotides of type B, with their 3'-ends, immediately or at a distance of up to 10 bases, adjoining the positions to be analyzed with regard to their methylation in the genomic DNA sample;

(d) the oligonucleotide (type B) having a known sequence of n nucleotides is elongated by means of a polymerase by at least one nucleotide, the nucleotide carrying a detectable label, and the elongation depending on the methylation status of the specific cytosine in the genomic DNA sample;

(e) the elongated oligonucleotides are analyzed for the presence of the label.

According to the invention it is preferred that the oligonucleotides (type B) are bonded to a solid phase at defined locations or that the amplificates are bonded to a solid phase at defined locations.

It is further preferred according to the invention that different oligonucleotide sequences are arranged on a plane solid phase in the form of a rectangular or hexagonal lattice. Herein it is preferred that the labels attached to the elongated oligonucleotides are identifiable at each position of the solid phase at which an oligonucleotide sequence is located.

According to the inventio it is further preferred that at least one primer (type A) is bonded to a solid phase during amplification.

In certain cases it is further preferred that different amplificates are arranged on the solid phase in the form of a rectangular or hexagonal lattice.

Furthermore it is preferred according to the invention that, prior to the amplification, the DNA is treated with a bisulfite solution (=disulfite, hydrogen sulfite).

According to the invention it is further preferred that the amplification is carried out by means of the polymerase chain reaction (PCR).

Furthermore it is preferred according to the invention that oligonucleotides of type A used either contain only the bases T, A and C or else the bases T, A und G and/or that the oligonucleotides of type B used either contain only the bases T, A and C or else the bases T, A und G.

According to the invention it is further preferred that the labels of the nucleotides are fluorescence labels.

Herein it is especially preferred that the labels of the nucleotides are radionuclides.

According to the invention it is also preferred that the labels of the nucleotides are detachable mass labels which are detected in a mass spectrometer.

Furthermore it is preferred according to the invention that the elongated oligonucleotides altogether are detected in the mass spectrometer, thus being uniquely labeled by their masses.

It is also preferred that in each case one fragment of the elongated oligonucleotides is detected in the mass spectrometer.

It is especially preferred according to the invention that the fragment of the elongated oligonucleotide is produced by digestion with one or several exo- or endonucleases.

Furthermore it is preferred according to the present invention that the produced fragments have a single positive or negative net charge for better detectability in the mass spectrometer.

It is particularly preferred that the detection of the elongated oligonucleotides is carried out and visualized by means of matrix assisted laser desorption/ionization mass spectrometry (MALDI) or using electron spray mass spectrometry (ESI).

The method according to the invention is also preferred if the polymerases are heat-resistant DNA-polymerases.

The method according to the invention is preferred as well, that SNPs are also detected and visualized in addition to the DNA methylation.

Accordingly preferred is the method as well, if the used nucleotides are terminating (type C 2) and/or chain-elongating nucleotides (type C 1).

A method according to the invention is also preferred wherein the chain-terminating nucleotide (type C 2) is selected from a group comprising either the bases T and C or else the bases G and A. and/or wherein the chain-elongating nucleotides (type C 1) are selected from a group comprising either the nucleobases A, T and C or else the bases G and A and T.

It is further preferred that the amplification of several DNA segments is carried out in one reaction vessel.

Furthermore it is preferred that the fluorescently labeled dCTP-derivate is Cy3-dCTP or Cy5-dCTP.

It is particularly preferred that solid phase surface is composed of silicon, glass, polystyrene, aluminum, steel, iron, copper, nickel, silver, or gold.

Furthermore a method is preferred wherein the genomic DNA is obtained from a DNA sample, sources of DNA comprising, e.g., cell lines, blood, sputum, stool, urine, cerebral-spinal fluid, tissue embedded in paraffin, histologic object slides, and all possible combinations thereof.

Finally a method is especially preferred wherein the methylation analyses of the upper and lower DNA strand is carried out.

Described is a method for detecting methylcytosine in genomic DNA samples:

The method includes the amplification, hybridization and elongation reaction of an entire DNA or of a fragment thereof. The method can be used for detecting methylcytosine and, at the same time, also of single nucleotide polymorphisms (SNPs) and mutations.

The genomic DNA to be analyzed is preferably obtained from usual sources of DNA such as cell lines, blood, sputum, stool, urine, cerebral-spinal fluid, tissue embedded in paraffin, histologic object slides, and all possible combinations thereof.

In the first step of the method, the used DNA is preferably treated with bisulfite (=disulfite, hydrogen sulfite) or else with another chemical in such a manner that all cytosine bases which are not methylated at the 5-position of the base are changed in such a manner that a different base results with regard to the base pairing behavior while the cytosines methylated at the 5-position remain unchanged. If bisulfite is used, then an addition takes place at the non-methylated cytosine bases. The subsequent alkaline hydrolysis then gives rise to the conversion of non-methylated cytosine nucleobases to uracil. The used genomic DNA is preferably fragmented using a restriction endonuclease prior to the chemical treatment.

In the second step of the method, the pretreated DNA is preferably amplified using a heat-resistant polymerase and at least one primer (type A). This primer can preferably contain 10-40 base pairs.

In a particularly preferred variant of the method, the amplification is carried out with primers of type A by means of the polymerase chain reaction (PCR).

In a preferred variant of the method, the amplification of several DNA fragments is carried out in one reaction vessel. This can either be a so-called "multiplex PCR" in which different primers each produce defined fragments. Different, defined amplifications are carried out in one reaction vessel. In a further, particularly preferred variant of the method, primers in each case selectively and reproducibly amplify several fragments. This is achieved, for example, in that the fragments bind, for example, to repetitive elements in the genome. In a particularly preferred variant of the method, the primers bind to transcription factor binding sites, to promoters or other reguor other regulatory elements in genes. In a particularly preferred variant of the method, the amplification is carried out by elongating primers which are bonded to a solid phase. A multiplex PCR in the broader sense can be carried out in that different primers are bonded at different, defined locations of a solid phase.

In an, again, preferred variant of the second method step, the solid phase is plane, the different oligonucleotide sequences being arranged in the form of a rectangular or hexagonal lattice. The result of this is that the different amplificates are arranged on the solid phase in the form of a rectangular or hexagonal lattice, as well. In this case, as already described above, several amplificates are directly produced on the solid phase.

The solid phase surface is preferably composed of silicon, glass, polystyrene, aluminum, steel, iron, copper, nickel, silver, or gold.

In a particularly preferred variant of the method, the oligonucleotides of type A either contain only bases T, A and C or only bases T, A und G.

In the third method step, the amplified genomic DNA is hybridized to at least one primer (type B), forming a duplex. The oligonucleotide, type B, preferably contains 10-35 base pairs. The hybridized oligonucleotides of type B, with their 3'-ends, immediately or at a distance of up to 10 bases, adjoin the positions to be analyzed with regard to their methylation in the genomic DNA sample.

The oligonucleotides which are hybridized to the amplificates can be bonded to a solid phase with their 5'-end, or at another base, or via their backbone but not via their 3'-end. Preferably, the binding occurs via the 5'-end. In a preferred variant, the solid phase is plane, the different oligonucleotide sequences (type B) being arranged in the form of a rectangular or hexagonal lattice.

The solid phase surface is preferably composed of silicon, glass, polystyrene, aluminum, steel, iron, copper, nickel, silver, or gold.

In a particularly preferred variant of the method, the oligonucleotides of type B either contain only bases T, A and C or only bases T, A und G.

In the fourth method step, the resulting oligonucleotide is elongated with a heat-resistant polymerase by at least one up to a maximum of ten nucleotides, at least one nucleotide carrying a detectable label. In this context, the type of elongation depends on the methylation status of the specific cytosine in the genomic DNA sample or else on possibly existing SNPs, point mutations or deletions, insertions and inversions.

In the case that the oligonucleotide of type B immediately adjoins the position to be analyzed, only terminating oligonucleotides (type C 2) are required. Depending on the sequence, however, chain-elongating oligonucleotides can be used as well provided that it is possible in the specific sequence context.

In a preferred variant of the method, the used nucleotides are terminating (type C 2) and/or chain-elongating nucleotides (type C 1). In this context, the terminating nucleotide (type C 2) is a 2',3'-didesoxynucleotide, and the chain-elongating nucleotide is a 2'-desoxynucleotide. In a particularly preferred variant of the method, the nucleobases of type C1 are selected from a group including bases T, A and C or else bases T, A and G. In a further, particularly preferred variant of the method, the nucleobases of type C2 are selected from a group including either bases T and C or else bases G and A.

The labeling of the elongated oligonucleotides of type B is preferably carried out via absorbing dyes and/or via chemiluminescence and/or via radioactive isotopes and/or via fluorescence labels which are introduced via the nucleotides added in the fourth method step. Also preferred is the labeling via the molecular mass of the elongated oligonucleotide. The fluorescence label is preferably inserted by a fluorescently labeled nucleotide such as Cy5-dCTP.

In the fifth method step, the elongated oligonucleotides are analyzed for the presence of a label. If a plane solid phase is used, then an analysis takes place at each location on the solid phase at which, originally, an oligonucleotide was immobilized.

In a particularly preferred variant of the method, the detection of the elongated oligonucleotides is carried out via their fluorescence. In this context, preferably, different elongation products have different fluorescence properties, which can be attained, for example by means of inserted nucleotides labeled with different dyes.

In a preferred variant of the method, fragments of the elongated oligonucleotide are produced by digestion with one or several exo- or endonucleases.

In a particularly preferred variant of the method, the labels of the nucleotides are detachable mass labels which are detectable in a mass spectrometer.

In a particularly preferred variant of the method, detachable mass labels, the elongated oligonucleotides altogether or fragments thereof are detected and visualized on the basis of their unique mass by means of matrix assisted laser desorption/ionization mass spectrometry (MALDI-MS) or using electron spray mass spectrometry (ESI).

The fragments detected in the mass spectrometer preferably have a single positive or negative net charge.

In a particularly preferred variant of the method, SNPs (single nucleotide polymorphisms) and cytosine methylations are analyzed in one experiment.

In a particularly preferred variant of the method, the lower and the upper strands of the DNA sample are analyzed in one experiment subsequent to the chemical pretreatment to ensure an internal experimental control.

A further subject matter of the present invention is a kit containing chemicals and aids for carrying out the bisulfite reaction and/or the amplification, the hybridization, the elongation reaction and/or polymerases and/or the documentation for carrying out the method.

EXAMPLE 1

A fragment of exon 23 of the factor VIII gene is given as an exemplary sequence.

In the first step, the fragment is amplified by primers of type A, namely by ATTATGTTGGAGTAGTAGAGTT-TAAATGGTT (SEQ-ID No. 1) and ACTTAACACTTAC-TATTTAAATCACAACCCAT (SEQ-ID No. 2). The amplified DNA is hybridized to an oligonucleotide of type B (for example, ATGTTGGATGTTGTTGAG (SEQ-ID No. 3)). Subsequently, the elongation reaction is carried out with 2',3'-didesoxycytidine triphosphate (ddCTP, as type C 2), 2',3'-didesoxythymidine triphosphate (ddTTP, as type C 2) and 2'-desoxyadenosine triphosphate (dATP, as type C 1). If a methylated cytosine was present, the elongation product ATGTTGGATGTTGTTGAGAAAC (SEQ-ID No. 4) is produced whereas the elongation product ATGTTGGATGT-TGTTGAGAAAT (SEQ-ID No. 5) is produced if a non-methylated cytosine is present in the sequence to be analyzed. Thus, different elongations arise which depend on the methylation status of the specific cytosine.

The terminating triphosphates of type C 2 can be labeled, for example, with two different dyes. This makes the elongation products distinguishable from each other. These different labels can, for example, be absorbing dyes such as Megaprime™ for ddTTP or Rediprime II™ for ddCTP.

EXAMPLE 2

A fragment of exon 23 of the factor VIII gene is given as an exemplary sequence.

In the first step, the fragment is amplified by primers of type A, namely by ATTATGTTGGAGTAGTAGAGTT-TAAATGGTT (SEQ-ID No. 1) and ACTTAACACTTAC-TATTTAAATCACAACCCAT (SEQ-ID No. 2). The amplified DNA is hybridized to a solid phase immobilized oligonucleotide of type B (for example, ATGTTGGATGT-TGTTGAG (SEQ-ID No. 3)). Subsequently, the elongation reaction is carried out with 2',3'-didesoxycytidine triphosphate (ddCTP, as type C 2), 2',3'-didesoxythymidine triphosphate (ddTTP, as type C 2) and 2'-desoxyadenosine triphosphate (dATP, as type C 1). If a methylated cytosine was present, the elongation product ATGTTGGATGTTGT-TGAGAAAC (SEQ-ID No. 4) is produced whereas the elongation product ATGTTGGATGTTGTTGAGAAAT (SEQ-ID No. 5) is produced if a non-methylated cytosine is present in the sequence to be analyzed. Thus, different elongations arise which depend on the methylation status of the specific cytosine.

The terminating triphosphates of type C 2 can be labeled, for example, with two different dyes. This makes the elongation products distinguishable from each other. These different labels can, for example, be absorbing dyes such as Megaprime™ for ddTTP or Rediprime II™ for ddCTP.

The invention claimed is:

1. A method for concurrently detecting 5-methylcytosine and SNP in genomic DNA samples, characterized in that the following steps are carried out:
   (a) chemically converting a genomic DNA from a DNA sample with a reagent, 5-methylcytosine and cytosine reacting differently, thus exhibiting different base pairing behaviors in the DNA duplex subsequent to the reaction;
   (b) amplifying the pretreated DNA using a polymerase and at least one oligonucleotide (type A) as a primer;
   (c) hybridizing the amplified genomic DNA to at least one oligonucleotide (type B), forming a duplex, said hybridized oligonucleotides of type B, with their 3'-ends, immediately or at a distance of up to 10 bases, adjoining the positions to be analyzed with regard to their methylation in the genomic DNA sample;
   (d) elongating the oligonucleotide (type B) having a known sequence of n nucleotides by means of a polymerase by a plurality of nucleotides, at least one nucleotide carrying a detectable label, and the elongation depending on the methylation status of the specific cytosine in the genomic DNA sample and on a single nucleotide polymorphism;
   (e) analyzing the elongated oligonucleotides for the presence of the label; and
   (f) deducing the presence of said 5-methylcytosine and SNP in the genomic DNA samples from the incorporated label.

2. The method as recited in claim 1, characterized in that the oligonucleotides (type B) are bonded to a solid phase at defined locations.

3. The method as recited in claim 1, characterized in that the amplificates are bonded to a solid phase at defined locations.

4. The method as recited in claim 2, characterized in that different oligonucleotide sequences are arranged on a plane solid phase in the form of a rectangular or hexagonal lattice.

5. The method as recited in claim 4, characterized in that the labels attached to the elongated oligonucleotides are identifiable at each position of the solid phase at which an oligonucleotide sequence is located.

6. The method as recited in claim 1, characterized in that at least one primer (type A) is bonded to a solid phase during amplification.

7. The method as recited in claim 1, characterized in that different amplificates are arranged on the solid phase in the form of a rectangular or hexagonal lattice.

8. The method as recited in claim 1, characterized in that, prior to the amplification, the DNA is treated with a bisulfite solution (=disulfite, hydrogen sulfite).

9. The method as recited in claim 1, characterized in that the amplification is carried out by means of the polymerase chain reaction (PCR).

10. The method as recited in claim 1, characterized in that the oligonucleotides of type A used either contain only the bases T, A and C or else the bases T, A and G.

11. The method as recited in claim 1, characterized in that the oligonucleotides of type B used either contain only the bases T, A and C or else the bases T, A and G.

12. The method as recited in claim 1, characterized in that the labels of the nucleotides are fluorescence labels.

13. The method as recited in claim 1, characterized in that the labels of the nucleotides are radionuclides.

14. The method as recited in claim 1, characterized in that the labels of the nucleotides are detachable mass labels which are detected in a mass spectrometer.

15. The method as recited in claim 1, characterized in that the elongated oligonucleotides altogether are detected in the mass spectrometer, thus being uniquely labeled by their masses.

16. The method as recited in claim 1, characterized in that in each case one fragment of the elongated oligonucleotides is detected in the mass spectrometer.

17. The method as recited in claim 15, characterized in that the fragment of the elongated oligonucleotide is produced by digestion with one or several exo- or endonucleases.

18. The method as recited in claim 16, characterized in that the produced fragments have a single positive or negative net charge for better detectability in the mass spectrometer.

19. The method as recited in claim 1, characterized in that the detection of the elongated oligonucleotides is carried out and visualized by means of matrix assisted laser desorption/ionization mass spectrometry (MALDI) or using electron spray mass spectrometry (ESI).

20. The method as recited in claim 1, wherein the polymerases are heat-resistant DNA-polymerases.

21. The method as recited in claim 1, wherein the used nucleotides are terminating (type C 2) and/or chain-elongating nucleotides (type C 1).

22. The method as recited in claim 21, wherein the chain-terminating nucleotide (type C 2) is selected from a group comprising either the bases T and C or else the bases G and A.

23. The method as recited in claim 21, wherein the chain-elongating nucleotides (type C 1) are selected from a group comprising either the nucleobases A, T and C or else the bases G and A and T.

24. The method as recited in claim 1, characterized in that the amplification of several DNA segments is carried out in one reaction vessel.

25. The method as recited in claim 23, characterized in that the fluorescently labeled dCTP-derivate is Cy3-dCTP or Cy5-dCTP.

26. The method as recited in claim 2, characterized in that solid phase surface is composed of silicon, glass, polystyrene, aluminum, steel, iron, copper, nickel, silver, or gold.

27. The method as recited in claim 1, wherein the genomic DNA is obtained from a DNA sample, sources of DNA comprising, e.g., cell lines, blood, sputum, stool, urine, cerebral-spinal fluid, tissue embedded in paraffin, histologic object slides, and all possible combinations thereof.

28. The method as recited in claim 1, characterized in that methylation analyses of the upper and lower DNA strands are carried out.

29. The method as recited in claim 1, wherein the oligonucleotide (type B) having a known sequence of n nucleotides is elongated by up to ten nucleotides.

* * * * *

SEQUENCE LISTING

```
<160> NUMBER OF SEQ ID NOS: 5

<210> SEQ ID NO 1
<211> LENGTH: 31
<212> TYPE: DNA
<213> ORGANISM: artificial sequence
<220> FEATURE:
<223> OTHER INFORMATION: oligonucleotide

<400> SEQUENCE: 1
attatgttgg agtagtagag tttaaatggt t                                 31

<210> SEQ ID NO 2
<211> LENGTH: 32
<212> TYPE: DNA
<213> ORGANISM: artificial sequence
<220> FEATURE:
<223> OTHER INFORMATION: oligonucleotide

<400> SEQUENCE: 2
acttaacact tactatttaa atcacaaccc at                                32

<210> SEQ ID NO 3
<211> LENGTH: 18
<212> TYPE: DNA
<213> ORGANISM: artificial sequence
<220> FEATURE:
<223> OTHER INFORMATION: oligonucleotide

<400> SEQUENCE: 3
atgttggatg ttgttgag                                                18

<210> SEQ ID NO 4
<211> LENGTH: 22
<212> TYPE: DNA
<213> ORGANISM: artificial sequence
<220> FEATURE:
<223> OTHER INFORMATION: oligonucleotide

<400> SEQUENCE: 4
atgttggatg ttgttgagaa ac                                           22

<210> SEQ ID NO 5
<211> LENGTH: 22
<212> TYPE: DNA
<213> ORGANISM: artificial sequence
```

```
<220> FEATURE:
<223> OTHER INFORMATION: oligonucleotide

<400> SEQUENCE: 5
atgttggatg ttgttgagaa at                                              22
```